United States Patent
Stack

(10) Patent No.: US 11,957,578 B2
(45) Date of Patent: Apr. 16, 2024

(54) DEVICE AND METHOD FOR PERCUTANEOUSLY DELIVERING A TRICUSPID VALVE

(71) Applicant: Synecor LLC, Durham, NC (US)

(72) Inventor: Richard S. Stack, Durham, NC (US)

(73) Assignee: Synecor LLC, Durham, NC (US)

( * ) Notice: Subject to any disclaimer, the term of this patent is extended or adjusted under 35 U.S.C. 154(b) by 58 days.

(21) Appl. No.: 17/551,156

(22) Filed: Dec. 14, 2021

(65) Prior Publication Data

US 2022/0183823 A1 Jun. 16, 2022

Related U.S. Application Data

(60) Provisional application No. 63/146,569, filed on Feb. 5, 2021, provisional application No. 63/125,298, filed on Dec. 14, 2020.

(51) Int. Cl.
*A61F 2/24* (2006.01)
*A61B 17/00* (2006.01)

(52) U.S. Cl.
CPC ........ *A61F 2/243* (2013.01); *A61B 17/00234* (2013.01); *A61B 2017/00292* (2013.01); *A61B 2017/00349* (2013.01)

(58) Field of Classification Search
CPC ...... A61F 2/243; A61F 2/2427; A61F 2/2433; A61F 2/2436; A61F 2/2439; A61B 17/00234; A61B 2017/00292; A61B 2017/00349
See application file for complete search history.

(56) References Cited

U.S. PATENT DOCUMENTS

| | | | |
|---|---|---|---|
| 2001/0044591 A1* | 11/2001 | Stevens | A61M 25/0662 604/6.14 |
| 2007/0156233 A1* | 7/2007 | Kapadia | A61F 2/2418 623/2.11 |
| 2011/0098720 A1* | 4/2011 | Taylor | A61B 17/221 606/129 |
| 2016/0113766 A1* | 4/2016 | Ganesan | A61F 2/2427 623/2.11 |
| 2016/0262887 A1* | 9/2016 | Chang | A61F 2/2466 |
| 2017/0312077 A1* | 11/2017 | Vidlund | A61F 2/2439 |
| 2018/0289473 A1 | 10/2018 | Rajagopal | |
| 2020/0121458 A1* | 4/2020 | Vidlund | A61F 2/2418 |
| 2021/0259830 A1* | 8/2021 | Enriquez-Sarano | A61F 2/2427 |

* cited by examiner

*Primary Examiner* — Jing Rui Ou

(57) ABSTRACT

To percutaneously deliver a replacement tricuspid valve, a cable is percutaneously positioned with a first end extending out of the venous vasculature at the neck, and a second end extending out of a femoral access point. An eyehook device is positioned over the first end. A tricuspid valve delivery device (TVDD) is advanced over the second end, and then advanced through an IVC into a right atrium. The eyehook device is advanced into the right ventricle, drawing an intermediate portion of the cable into the right ventricle. Contact between the distal end of the eyehook device and the right ventricle is maintained while the TVDD is pushed from the femoral vein. The intermediate portion of cable applies a force to a distal nose of the TVDD that causes the distal nose to be steered into a tricuspid valve annulus as the TVDD is advanced.

9 Claims, 8 Drawing Sheets

102

DEVICE AND METHOD FOR PERCUTANEOUSLY DELIVERING A TRICUSPID VALVE

This application claims the benefit of U.S. Provisional Application 63/125,298, filed Dec. 14, 2020 and U.S. Provisional Application 63/146,569, filed Feb. 5, 2021.

BACKGROUND

Few minimally invasive techniques for treating the tricuspid valve are currently available. While desirable, the ability to percutaneously deliver a replacement tricuspid valve is a particular challenge that has not yet found a suitable solution, due in part to the large proportions and stiffness of a delivery system carrying a tricuspid valve replacement.

Co-pending and commonly owned U.S. application Ser. No. 17/173,158, filed Feb. 10, 2021 and incorporated herein by reference, describes a system and method for percutaneously delivering a replacement tricuspid valve to a heart. As described in that application, a wire is percutaneously introduced into the venous vasculature. A distal end of the wire is passed into a right atrium, through a tricuspid valve ring, and into a right ventricle, within which it is anchored to tissue of the right ventricle. A tricuspid valve delivery device carrying a replacement tricuspid valve is positioned over the wire, and a director is positioned over the wire proximally adjacent to, and in contact with, the tricuspid valve delivery device. The director and delivery device are pushed over the wire into the right atrium while traction is applied traction to the wire that is fixed within the right ventricle. The director is actively articulated during advancement, to articulate the replacement tricuspid valve on the valve delivery device within a tricuspid valve ring of the heart.

In the prior application, the wire is anchored to tissue using screwing, clipping, or other means. The present application describes an alternative system and method for use in delivering a tricuspid valve delivery system carrying a tricuspid valve replacement device to the tricuspid valve annulus. The alternative system and method described in this application avoids the need for anchoring the wire to tissue.

DETAILED DESCRIPTION

The system and method described below allow percutaneous delivery of a replacement valve using an access point in the venous vasculature, such as a femoral vein. In use the system facilitates movement of the replacement valve from the access point, through the inferior vena cava (IVC) to the right atrium (RA), allowing articulation of the assembly through the acute angle needed to properly orient the replacement valve within the native valve ring.

System

Figure 1:
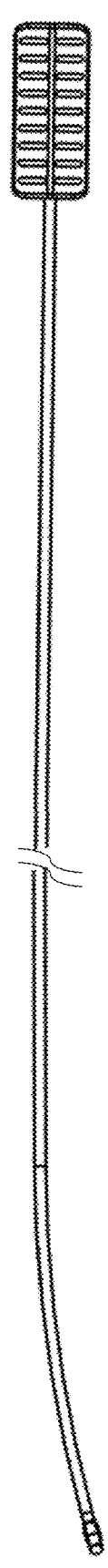
FIGS. 1 and 2 are a side elevation view and a plan view, respectively, of an eye loop device used in the disclosed system.
Figure 2:
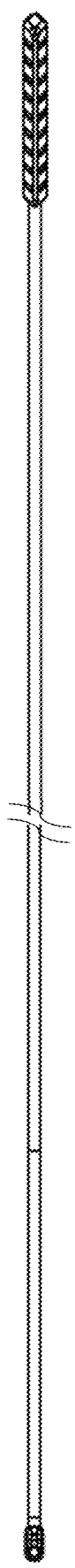
Figure 5:
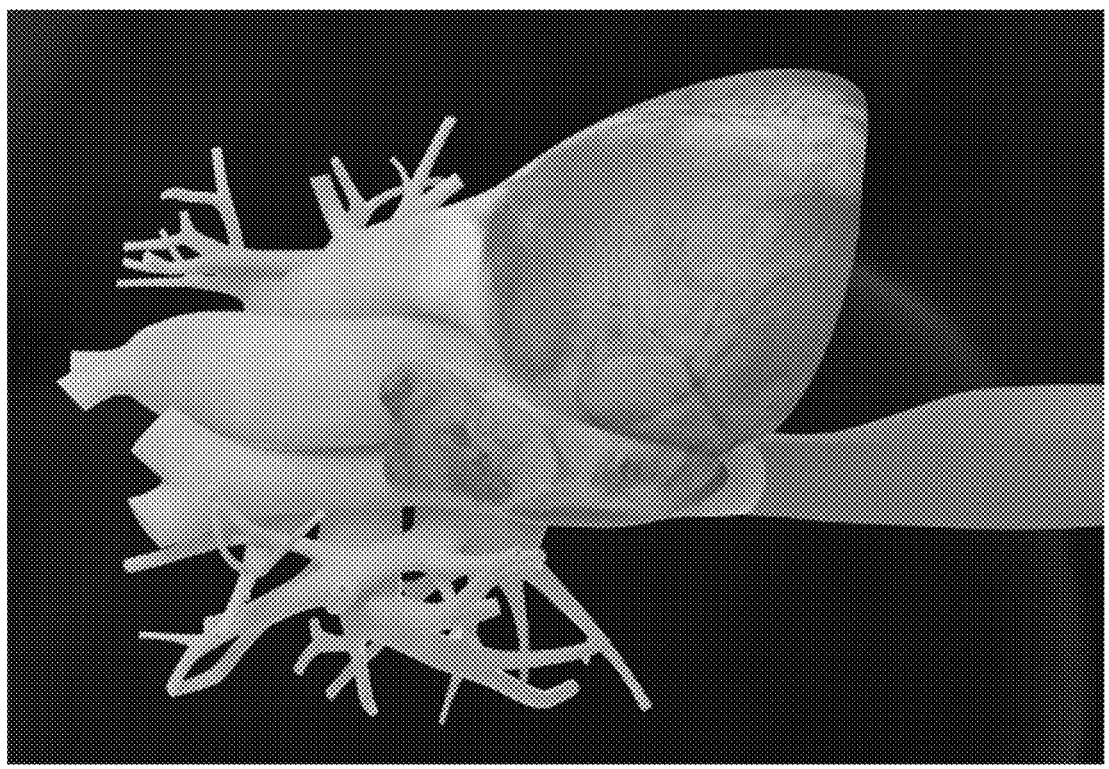
FIG. 5 shows an anterior view of the heart.
Figure 3A:
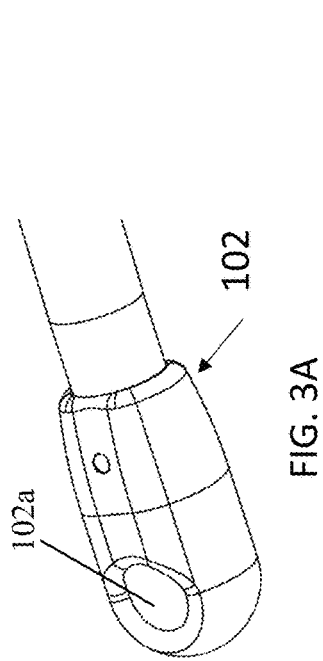
FIG. 3A is a perspective view of the distal end of the eye loop device.
Figure 3B:
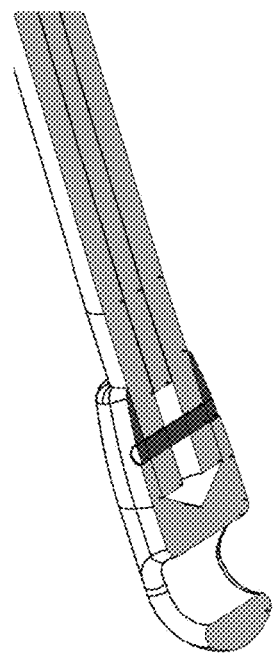
FIG. 3B is a cross-section view of the distal end of the eye loop device.
Figure 4:
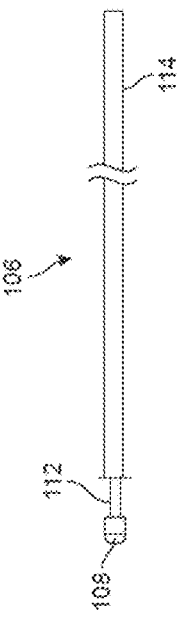
FIG. 4 is a side elevation view of a cable used in the disclosed system.

Components of an embodiment of the disclosed system include an eye hook/eyelet device 102 (FIGS. 1-3B), a tricuspid valve (TV) delivery system 104 that carries a tricuspid replacement valve (FIGS. 11-16) and a cable 106 (FIG. 4). The TV delivery system 104 is advanceable over the cable 106.

The eye hook device 102 comprises an elongate shaft with an opening or eyelet 102a at its distal end. The opening is preferably a lateral opening in the eye hook device that is transverse to the longitudinal axis of the eye hook device. It may be the opening of a loop at the distal end of the shaft. The opening is proportioned to receive the cable. The shaft of the eye hook device is formed using sufficient column strength to withstand the forces described below in connection with the steps illustrated in FIGS. 12 through 14, without buckling or bending.

The cable 106 and/or the inner walls of the opening 102a are designed to minimize resistance to passage of the cable through the opening, and one or both may be formed with highly lubricious coatings. The opening of the eyelet may include chamfered edges as shown to further minimize friction on the cable.

Figure 7:
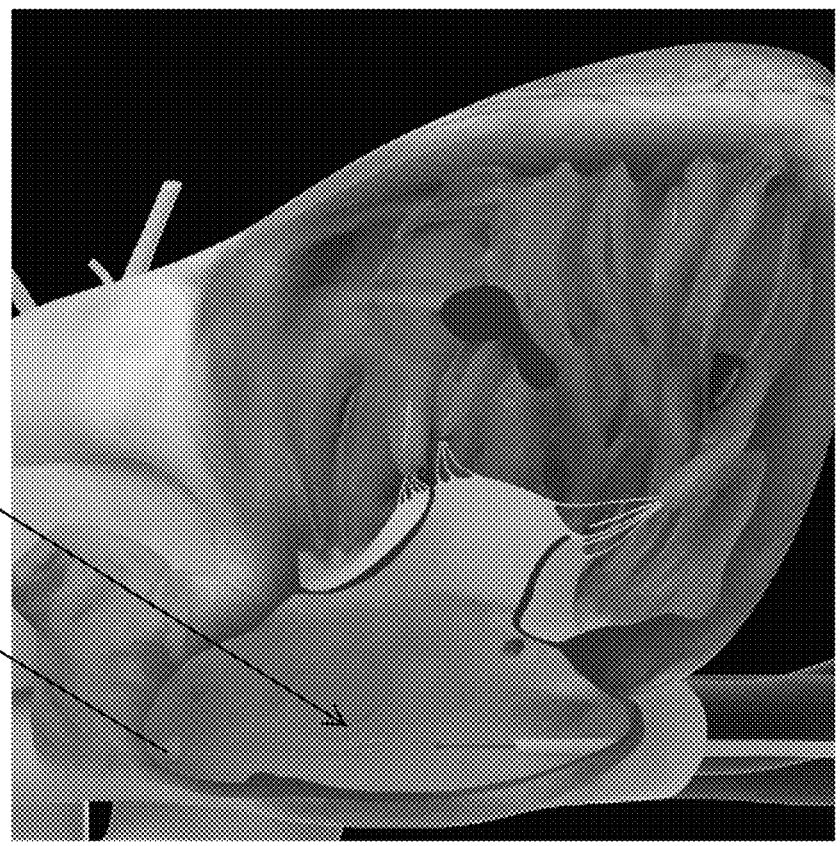
FIGS. 6 through 17 show the anterior view of the heart shown in FIG. 5, with the right atrium and right ventricle cut away, and further show the steps of the disclosed method.

The cable 106 comprises an elongate cable 112 having a distal end with a tip element 108 suitable for being grasped using a snare 110 (FIG. 7). A lubricious polymer coating 114 (e.g., PEBA) covers the cable shaft 112, leaving a gap between each end of the coating and the tip element 108. This allows room between the tip element and coating 114 for a snare 110 to seat when engaging the tip element.

The cable is of sufficient length to extend from outside the body through a percutaneous sheath or multi-purpose catheter C1 in the right femoral vein (RFV), through the inferior vena cava (IVC), superior vena cava (SVC) and out of the body through a second percutaneous sheath or multipurpose catheter C2 in the internal jugular vein in the neck. Note that the term "cable" is not intended to mean that the cable must be formed using any particular type of construction. This term is used broadly in this application to represent any sort of wire, filament, tendon, cable, or other elongate element

Method

Figure 6:
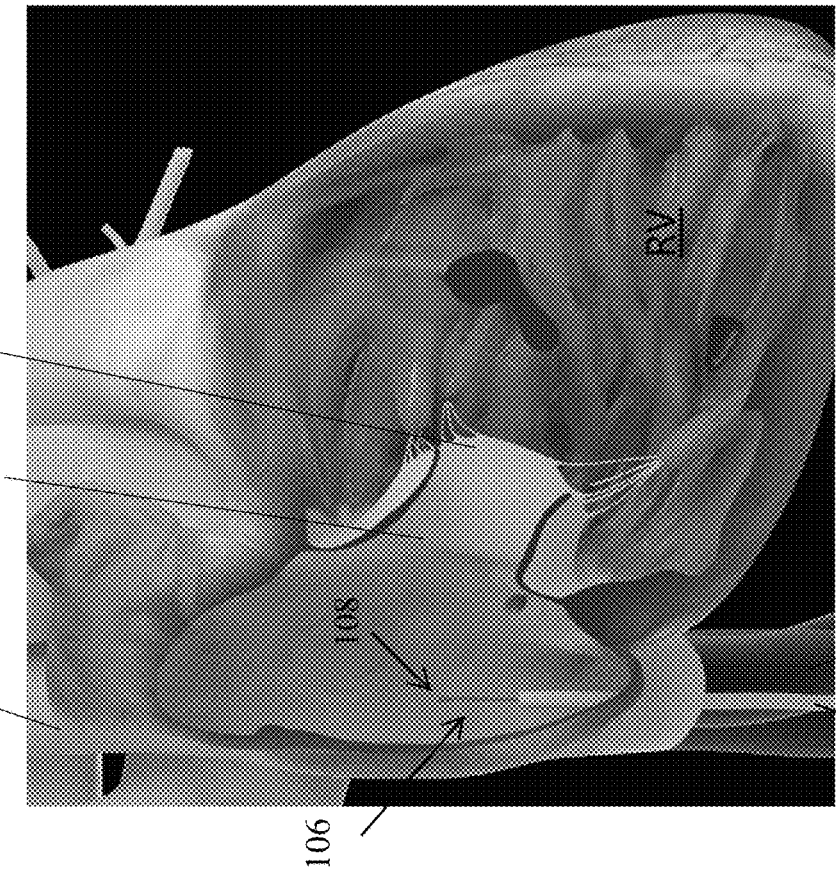

A method of using the system will next be described. Referring to FIGS. 6 and 7, the tip element 108 of the cable 106 is introduced into the percutaneous catheter positioned in the RFV and advanced to the IVC. Snare 110 is introduced through the percutaneous catheter positioned in the internal jugular vein, through the SVC, and is used to capture the tip element 108. The snare is withdrawn to draw the tip end of the cable out of the body. In alternative embodiments, this step may be reversed, with the cable introduced at the neck and captured by a snare introduced via the femoral access point.

Figure 9:
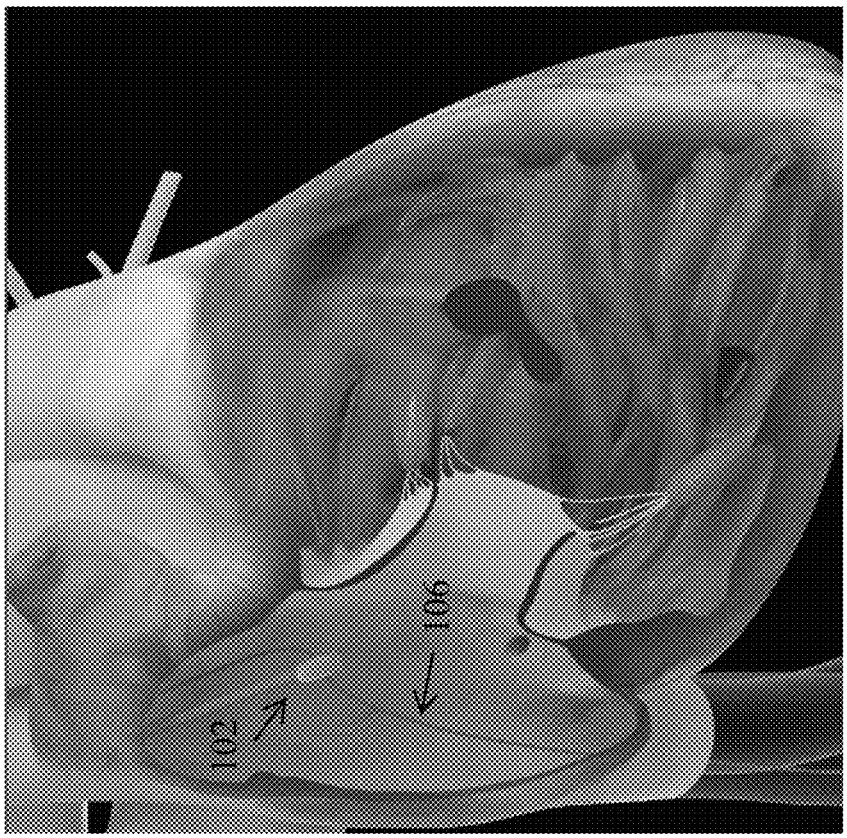
Figure 8:
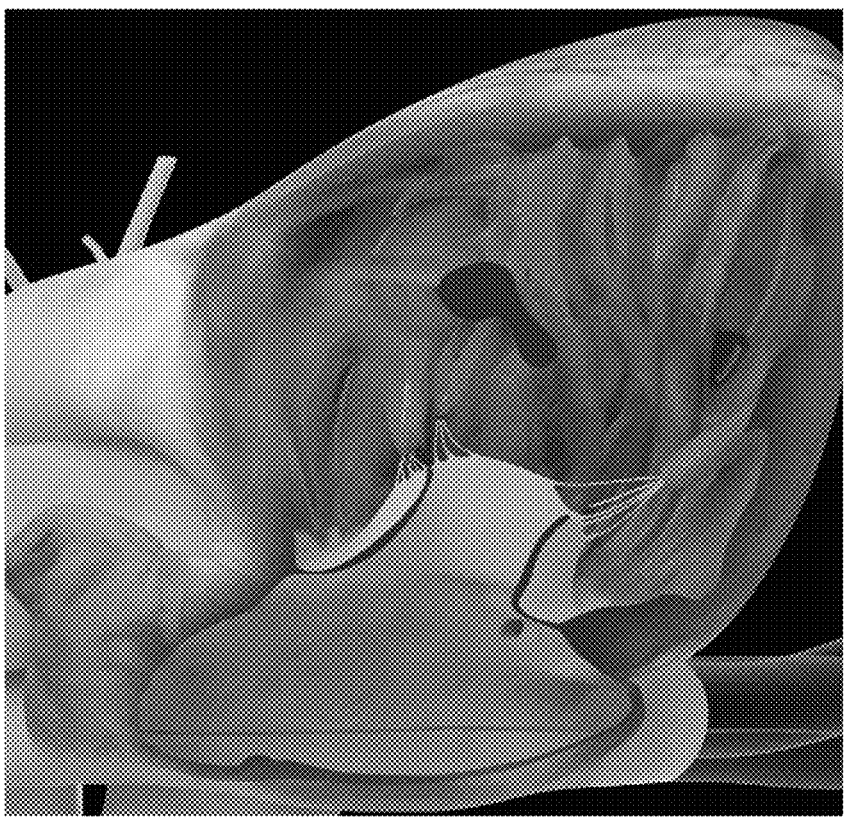

Outside the body at the neck, the opening in the eye hook is threaded over the tip end 108 of the cable and then advanced over the cable into the percutaneous catheter in the internal jugular vein (IJ). The eye hook is advanced over the cable until it reaches the right atrium (RA), as shown in FIG. 9.

Figure 11:
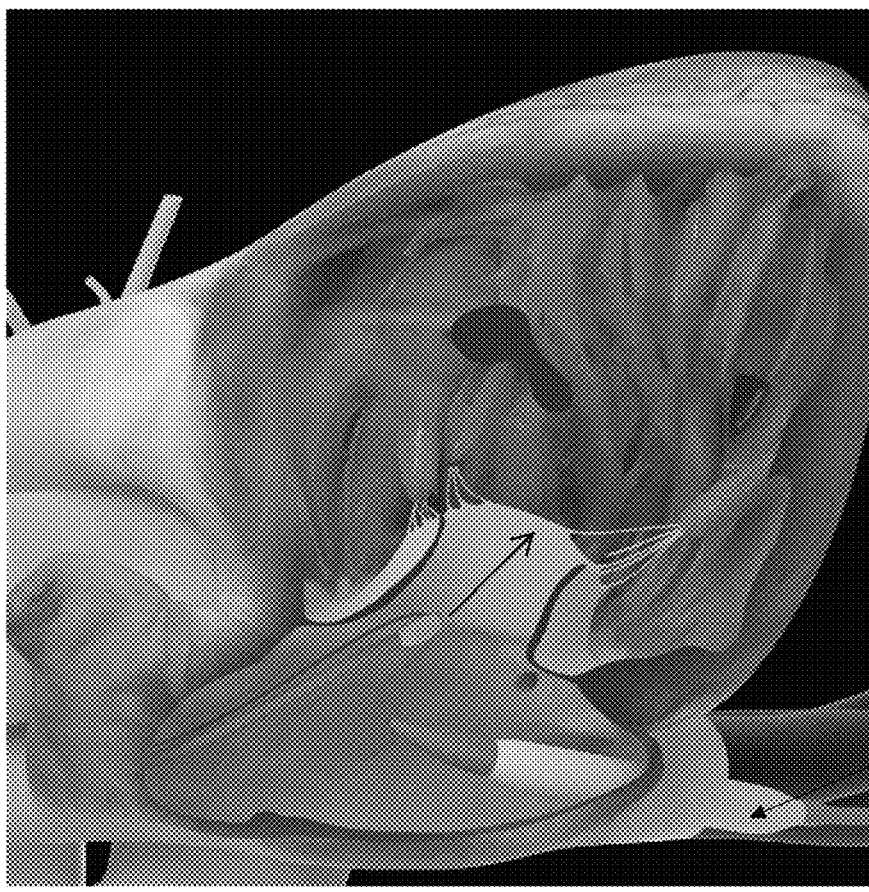
Figure 10:
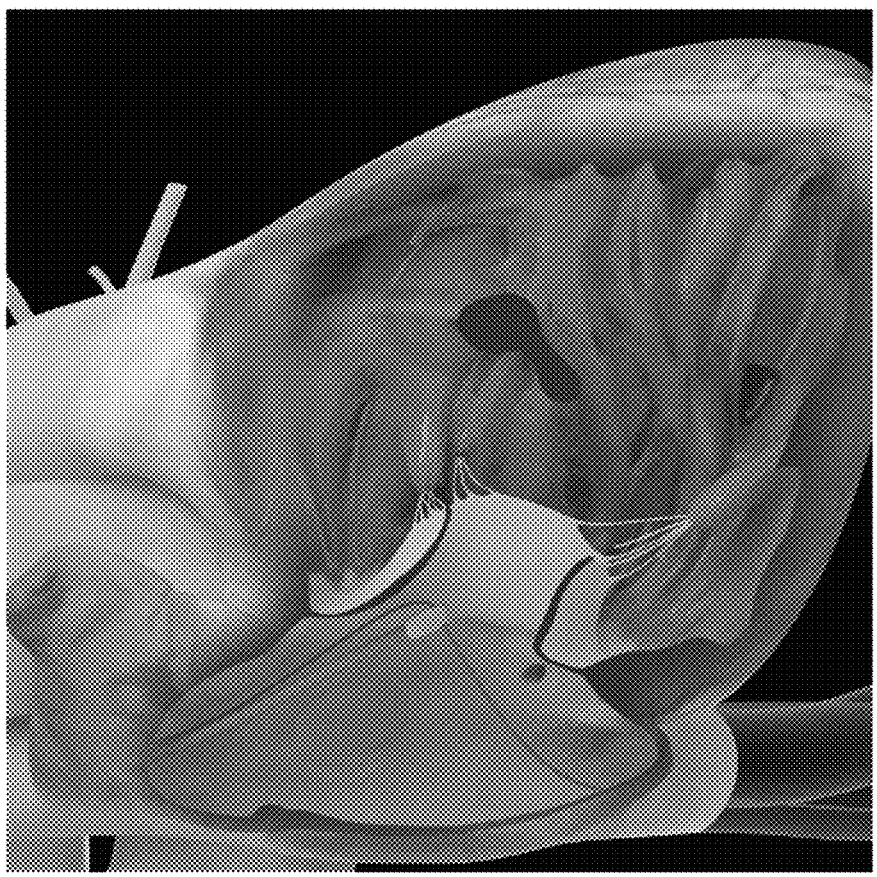
Figure 12:
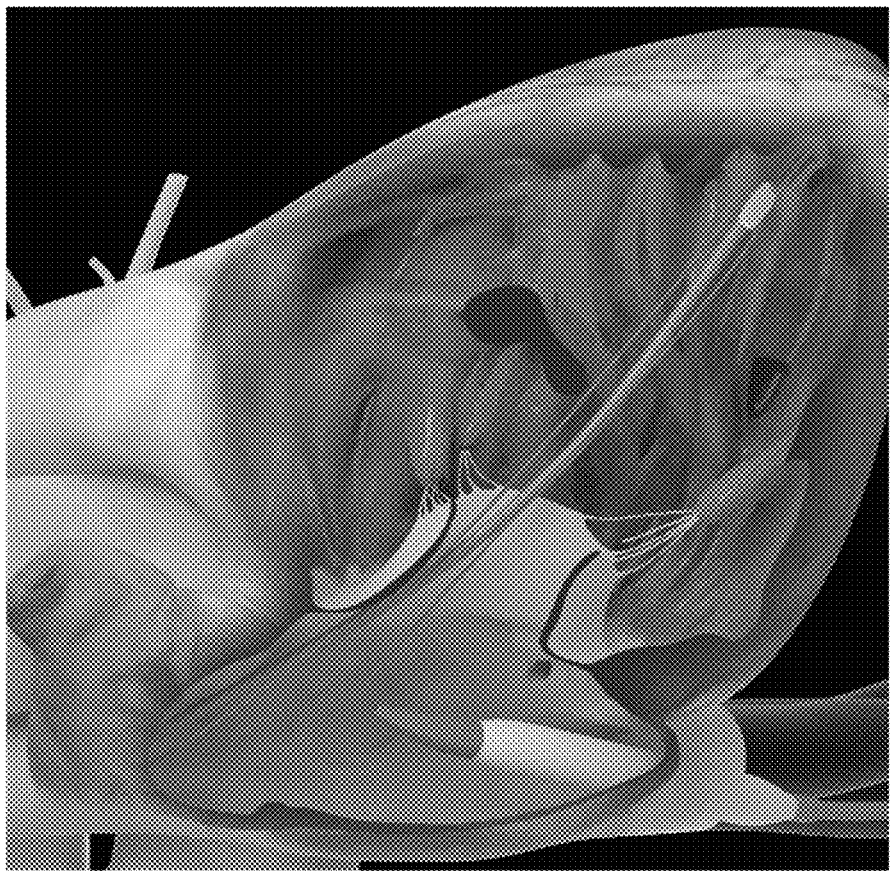

Outside the body, the distal nose of the TV delivery system 104 is advanced over and locked onto the opposite end of the cable, which extends out of the body from the catheter positioned in the RFV. The TV delivery system 104 is advanced from the RFV into the IVC by pushing the TV delivery system and pulling on the cable from outside the neck as needed. Once the delivery system 104 reaches the heart, slack is created in the cable to permit the eye hook to be advanced to the RV apex as shown in FIGS. 11 and 12.

Figure 13:
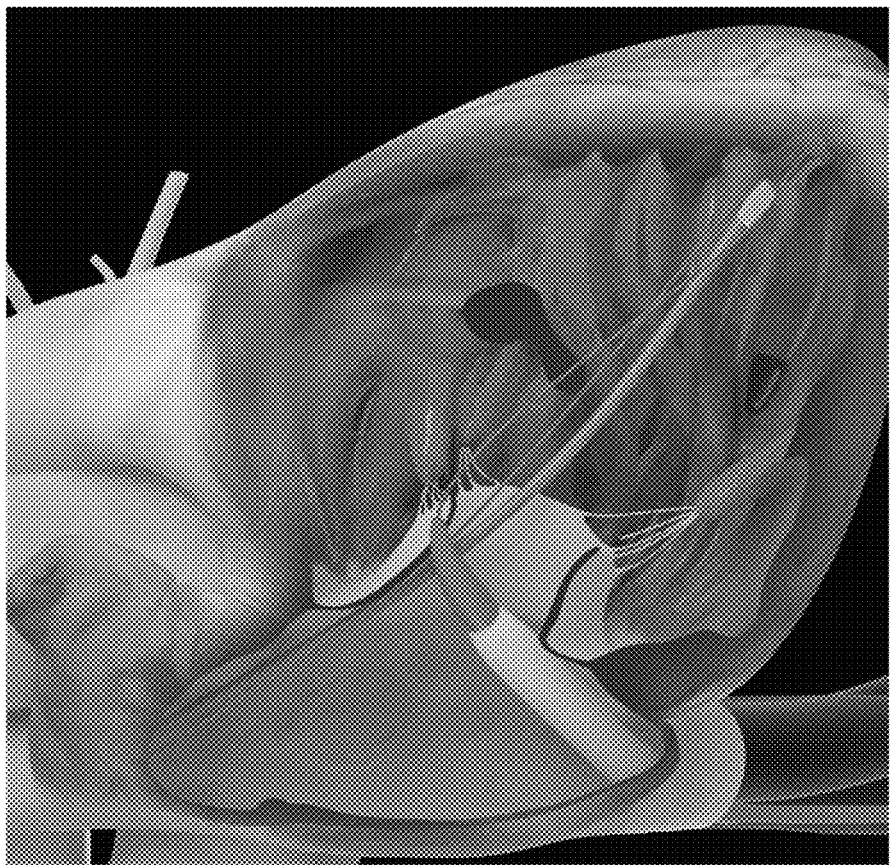
Figure 14:
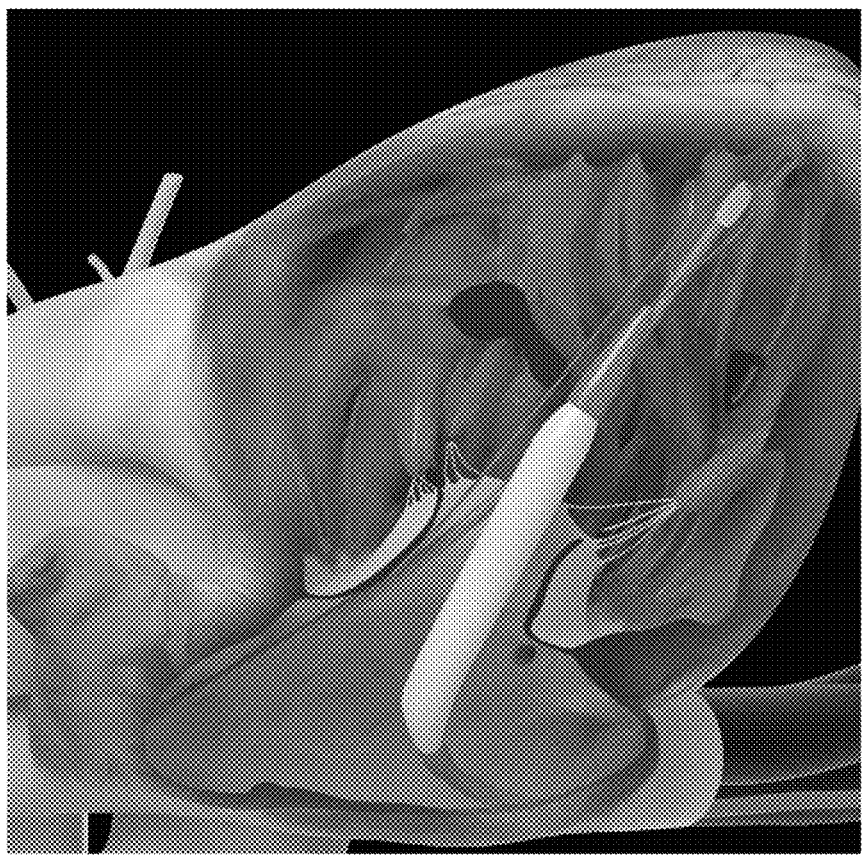
Figure 17:
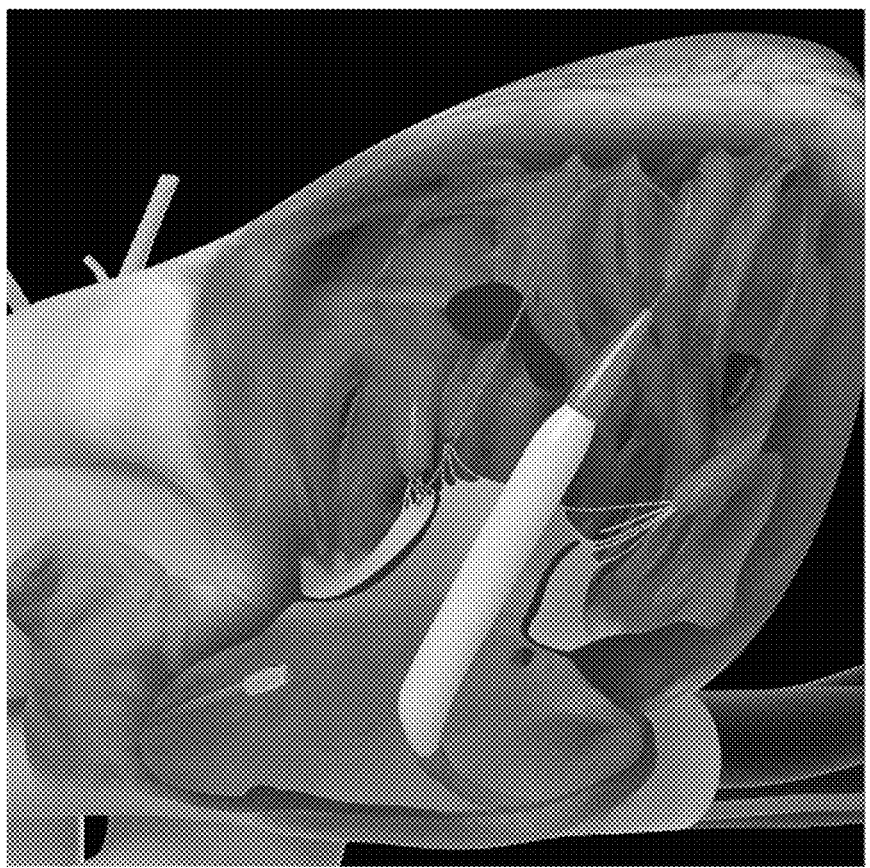

Referring to FIGS. 13 and 14, the TV delivery system is further pushed from the RFV as the cable is strongly pulled from the neck. During this step, firm pressure is applied to the shaft of the eye hook device from outside the neck to keep the eye hook seated at the RV apex. Thus, as a result of the pulling forces applied to the cable at the neck, the cable draws the nose of the TV delivery device downwardly in the direction of the RV apex as it crosses the TV annulus, allowing the TV delivery system to pass safely into the RV without contacting the opposite edge of the tricuspid valve annulus.

Figure 15:
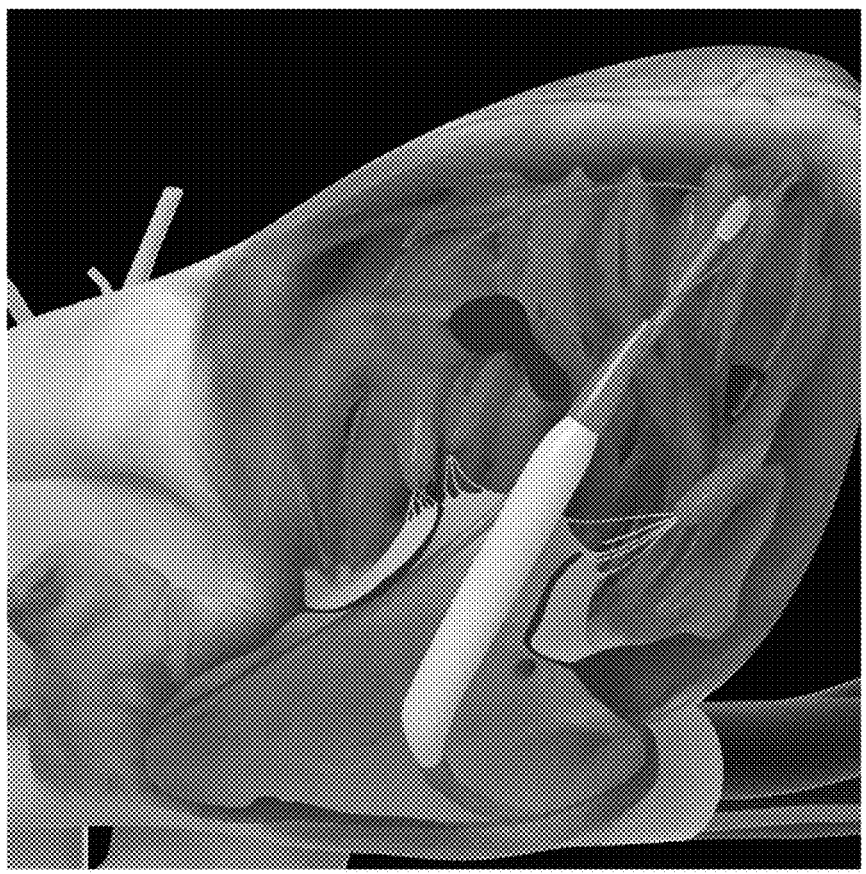
Figure 16:
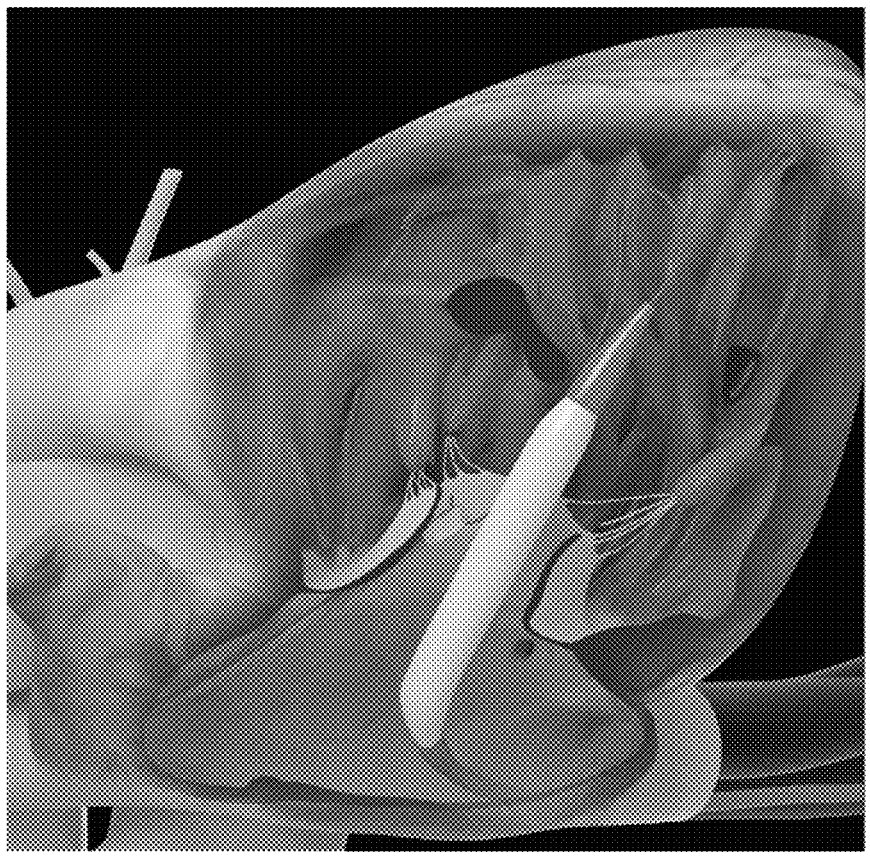

Once the TV delivery system is at the target site for deployment of the valve, the cable is unlocked from the back end of the TV delivery system and is pulled from the RFV, causing the cable end that had been extending from the neck to pass into the heart as shown in FIG. 15. The eye hook is withdrawn, causing the cable to slip out of the opening in the eye hook as shown in FIG. 16, and is removed via the neck. The TV is deployed from the delivery system, with the free end of cable extending from the distal part of the TV heart serving to protect the walls of the RV from the tip of the TV delivery system during deployment. Finally, the cable and delivery system are withdrawn via the RFV.

The system and method described in this application may be combined with concepts described in commonly owned U.S. application Ser. No. 17/173,158, filed Feb. 10, 2021.

All prior patents and applications referred to herein, including for purposes of priority, are incorporated herein by reference.

I claim:

1. A method of percutaneously delivering a replacement tricuspid valve to a heart, comprising:
    positioning a cable such that a first end of the cable extends out of a venous vasculature via a percutaneous opening superior to the heart, and such that a second end of the cable extends out of the venous vasculature via a percutaneous opening inferior to the heart;
    positioning an eyelet disposed at a distal end of an eyelet device over the first end of the cable;
    positioning a tricuspid valve delivery device over the second end of the cable, the tricuspid valve delivery device carrying a replacement tricuspid valve;
    advancing the tricuspid valve delivery device through an inferior vena cava into a right atrium;
    advancing the distal end of the eyelet device, with the cable extending through the eyelet, through a tricuspid valve annulus and into contact with a right ventricle, such that a portion of the cable extends into the right ventricle;
    while maintaining contact between the distal end of the eyelet device and the right ventricle, advancing the tricuspid valve delivery device, wherein the portion of cable extending into the right ventricle applies a force to a distal nose of the tricuspid valve delivery device, said force steering the distal nose into the tricuspid valve annulus;
    using the tricuspid valve delivery device, expanding the replacement tricuspid valve within the tricuspid valve annulus; and
    removing the eyelet device and the cable from the heart.

2. The method of claim 1, wherein advancing the distal end of the eyelet device into contact with the right ventricle advances the distal end of the eyelet device into contact with a right ventricular apex.

3. The method of claim 1, wherein advancing the tricuspid valve delivery device through an inferior vena cava into a right atrium is performed while applying traction to the first end of the cable.

4. The method of claim 1, wherein advancing the tricuspid valve delivery while maintaining contact between the distal end of the eyelet device and the right ventricle is performed while applying traction to the first end of the cable.

5. The method of claim 1, wherein positioning the tricuspid valve delivery device over the second end of the cable includes releasably fixing the tricuspid valve delivery device to the cable, and wherein advancing the tricuspid valve delivery device through an inferior vena cava into a right atrium includes simultaneously advancing the tricuspid valve delivery device and the cable.

6. The method of claim 1, wherein positioning the tricuspid valve delivery device over the second end of the cable includes releasably fixing the tricuspid valve delivery device to the cable, and wherein advancing the tricuspid valve delivery while maintaining contact between the distal end of the eyelet device and the right ventricle includes simultaneously advancing the tricuspid valve delivery device and the cable.

7. The method of claim 1, wherein positioning the cable includes introducing the first end of the cable into a percutaneous access point to a femoral vein, introducing a snare into a superior vena cava via a venous access point superior to the heart, capturing the first end of the cable using a snare, and withdrawing the snare to withdraw the first end out the venous access point superior to the heart.

8. The method of claim 1, wherein positioning the cable includes introducing the second end of the cable into a superior vena cava via a venous access point superior to the heart, capturing the second end of the cable using a snare, and withdrawing the snare to withdraw the second end out the percutaneous access point to the femoral vein.

9. The method of claim 1, wherein maintaining contact comprises pushing the distal end of the eyelet device in a distal direction to prevent forces from the cable from causing the distal end to separate from a wall of the right ventricle.

* * * * *